United States Patent [19]

Suhara et al.

[11] 4,204,044

[45] May 20, 1980

[54] PROCESS FOR THE MANUFACTURE OF OPTICALLY ACTIVE α-HYDROXYCARBOXYLIC ACIDS

[75] Inventors: Yasuji Suhara; Hiromi Maruyama, both of Yokohama; Toyoaki Sawada, Zushi; Mayumi Ogawa, Kamakura; Kazuteru Yokose, Urayasu; Morio Fujiu, Tokyo; Kimihiro Watanabe, Ayase, all of Japan

[73] Assignee: Hoffmann-La Roche Inc., Nutley, N.J.

[21] Appl. No.: 926,592

[22] Filed: Jul. 19, 1978

[30] Foreign Application Priority Data

Jul. 26, 1977 [CH] Switzerland .................... 9218/77

[51] Int. Cl.$^2$ .............................................. C12D 1/02

[52] U.S. Cl. ........................................... 435/280; 435/837; 435/843; 435/832; 435/876; 435/877; 435/886

[58] Field of Search ..................... 195/2, 30; 435/280

[56] References Cited

U.S. PATENT DOCUMENTS

3,823,069   7/1974   Miyaki et al. .................... 195/2

OTHER PUBLICATIONS

Chemical Abstracts, vol. 47, 1953, 3366i.

*Primary Examiner*—Lionel M. Shapiro
*Attorney, Agent, or Firm*—Jon S. Saxe; Bernard S. Leon; William H. Epstein

[57] ABSTRACT

The present invention is concerned with a process for the manufacture of optically active α-hydroxycarboxylic acids, especially a process for the manufacture of optically pure D- or L-α-hydroxycarboxylic acids.

9 Claims, No Drawings

PROCESS FOR THE MANUFACTURE OF OPTICALLY ACTIVE α-HYDROXYCARBOXYLIC ACIDS

BACKGROUND OF THE INVENTION

The manufacture of optically active α-hydroxycarboxylic acids has hitherto been carried out by optical resolution of D,L-α-hydroxycarboxylic acids with resolving agents such as optically active amines; see for example J.Chem.Soc. (1906) 89, 935 relating to the optical resolution of D,L-lactic acid with morphine.

These known processes have, however, been found to be inefficient, especially because the resolving agents are costly and the separation is complicated.

DESCRIPTION OF THE INVENTION

The process provided by the present invention enables optically pure α-hydroxycarboxylic acids to be manufactured in high yield and in a very simple manner. This process comprises asymmetrically dehydrogenating a D,L-α-hydroxycarboxylic acid of the general formula

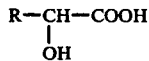    I wherein R represents a branched-chain or straight-chain alkyl group containing 1–13 C-atoms or a pyridyl group, or a salt thereof to the α-ketocarboxylic acid or to a salt thereof by means of a microorganism belonging to the genus Streptomyces, Pseudomonas or Bacillus or to the Coryne-form group and having enantiospecific dehydrogenase activity, liberating the acid from a resulting salt and isolating the non-dehydrogenated enantiomer of the α-hydroxycarboxylic acid and, if desired, the α-ketocarboxylic acid from the medium.

According to a preferred embodiment of the process provided by the present invention, the α-ketocarboxylic acid obtained is reduced in a manner known per se to the α-hydroxycarboxylic acid which is recycled into the process as the starting material.

Typical examples of racemic α-hydroxycarboxylic acids of formula I hereinbefore are 2-hydroxypropionic acid, 2-hydroxybutyric acid, 2-hydroxyvaleric acid, 2-hydroxy-3-methylbutyric acid, 2-hydroxycaproic acid, 2-hydroxy-4-methylvaleric acid, 2-hydroxy-3,3-dimethylbutyric acid, 2-hydroxyheptylic acid, 2-hydroxy-4-methylcaproic acid, 2-hydroxycaprylic acid, 2-hydroxypelargonic acid, 2-hydroxydecanoic acid, 2-hydroxyundecanoic acid, 2-hydroxydodecanoic acid, 2-hydroxytridecanoic acid, 2-hydroxytetradecanoic acid, 2-hydroxypentadecanoic acid, α-hydroxy-3-pyridylacetic acid and the like.

The microorganism used in the process provided by the present invention is a microorganism having enantiospecific dehydrogenase activity and belonging to the genus Streptomyces, Pseudomonas or Bacillus or to the Coryne-form group. The expression "enantiospecific dehydrogenase activity" used herein signifies the capability to convert selectively one of the enantiomers of a D,L-α-hydroxycarboxylic acid of formula I or a salt thereof by asymmetric dehydrogenation into the corresponding α-ketocarboxylic acid or a salt thereof, while the other enantiomer usually remains in the form of an optically active α-hydroxycarboxylic acid or a salt thereof. The microorganism can be used in the form of the culture broth or in the form of an extract thereof.

Preferred strains which can be used in the process provided by the present invention are the following bacteria and actinomycetes isolated from soil samples from various districts of Japan, as well as related strains and variants thereof. In the following Tables there are given the taxonomical characteristics of such bacteria as well as the locality from which the soil samples were obtained. All bacteria mentioned in these Tables have been deposited in the Fermentation Research Institute, Agency of Industrial Science and Technology, Chiba, Japan under the given FERM-P numbers. Corresponding cultures are likewise deposited in the USA; the NRRL numbers relating to cultures deposited in the United States Department for Agriculture, Northern Utilization Research and Development Division, Peoria, Ill., and the ATCC numbers relating to cultures deposited in the American Type Culture Collection, Rockville, Md.

| | A-1) Morphological characteristics and culture characteristics of gram-positive, spore-forming bacilli | | |
|---|---|---|---|
| Characteristics | Strain NRS-85KH20B (FERM-P No. 3164) (NRRL B-11084) | NRS-112KH25B (FERM-P No. 3165) (NRRL 11085) | NRS-137KH20B FERM-P No. 3169) (ATCC 31301) |
| a) Morphology | | | |
| 1 Form | bacilli | bacilli | bacilli |
| 2 Size (μ) | 1.4–1.8×2.0–4.0 | 0.8–1.2×3.0–7.0 | 0.5–1.0×1.5–4.0 |
| 3 Pleomorphism | — | — | — |
| 4 Motility | (−) | + | + |
| 5 Spores | + | + | + |
| (I) Size (μ) | 0.8–1.0×1.5–2.0 | 0.8–1.0×1.5–2.0 | 0.4–0.8×0.8–1.2 |
| (II) Form | elliptical | elliptical | elliptical |
| (III) Extension of the sporangium | — | — | — |
| (IV) Position | central | central | central |
| 6 gram staining | + | + | + |
| 7 Acid-fast staining colouring | — | — | — |
| b) Culture characteristics | | | |
| 1 Nutrient agar-plate Form | convex, entirely smooth | flat, undulating rough | flat, schizoid rough |

-continued

| A-1) Morphological characteristics and culture characteristics of gram-positive, spore-forming bacilli | | | |
|---|---|---|---|
| Strain<br>Characteristics | NRS-85KH20B<br>(FERM-P No. 3164)<br>(NRRL B-11084) | NRS-112KH25B<br>(FERM-P No. 3165)<br>(NRRL 11085) | NRS-137KH20B<br>FERM-P No. 3169)<br>(ATCC 31301) |
| Opacity | translucent | opaque | translucent |
| Colour of colony | pale yellow to pale brown | cream | pale yellow to cream |
| Soluble pigment | faint brown | none | none |
| 2 Nutrient agar slant | | | |
| Growth | abundant | abundant | moderate |
| Form | filiform | spreading | echinulate |
| Lustre | dull | dull | dull |
| Colour of colony | cream to pale brown | cream-white | pale brown to orange |
| Soluble pigment | brown | none | none |
| 3 Bouillon liquid | | | |
| Growth | moderate | moderate | abundant |
| Surface-growth | abundant | none | scant |
| Precipitate | scant | abundant | moderate |
| Pigmetation | none | none | none |
| 4 Gelatine stab culture | | | |
| Growth | abundant | very abundant | abundant |
| Liquefaction | + | + | + |
| 5 Litmus milk | | | |
| Litmus | − | − | alkaline |
| Peptonisation | + | + | − |
| Coagulation | − | − | − |

| A-2 Physiological characteristics of gram-positive, spore-forming bacilli | | | | | | |
|---|---|---|---|---|---|---|
| Strain<br>Characteristics | NRS-85KH20B<br>(FERM-P<br>No. 3164)<br>(NRRL B-11084) | | NRS-112KH25B<br>(FERM-P)<br>No. 3165)<br>NRRL 11085) | | NRS-137KH20B<br>(FERM-P)<br>No. 3169)<br>(ATCC 31301) | |
| c) Physiological characteristics | | | | | | |
| 1 Nitrate reduction | − | | + | | + | |
| 2 Nitrate respiration | − | | − | | − | |
| 3 MR-test | − | | + | | − | |
| 4 VP-test | − | | − | | − | |
| 5 Indole production | − | | − | | − | |
| 6 $H_2S$-production | − | | − | | − | |
| 7 Starch hydrolysis | + | | + | | − | |
| 8 Citrate utilisation | | | | | | |
| a. Koser medium | + | | + | | + | |
| b. Christensen medium | + | | − | | + | |
| 9 Utilisation of | | | | | | |
| $NaNO_3$ | + | | + | | + | |
| $(NH_4)_2SO_4$ | + | | + | | + | |
| Urea | + | | + | | + | |
| Na glutamate | + | | + | | + | |
| 10 Pigment formation | +(insoluble) | | − | | − | |
| 11 Urease | − | | − | | + | |
| 12 Oxidase | + | | + | | + | |
| 13 Catalase | + | | + | | + | |
| 14 Growth range | | | | | | |
| pH | 5.0–9.5 | | 5.0–10.0 | | 5.0–10.0 | |
| Temperature | 20° C.–45° C. | | 20° C.–37° C. | | 10° C.–40° C. | |
| 15 Aerobic growth | + | | + | | + | |
| Anaerobic growth | + | | + | | + | |
| 16 O-F test | fermentation | | fermentation | | fermentation | |
| 17 Acid and gas | acid | gas | acid | gas | acid | gas |
| 1) L-arabinose | + | − | − | − | − | − |
| 2) D-xylose | + | − | − | − | − | − |
| 3) D-glucose | + | − | + | − | − | − |
| 4) D-mannose | − | − | − | − | − | − |
| 5) D-fructose | + | − | + | − | − | − |
| 6) D-galactose | + | − | − | − | − | − |
| 7) Maltose | + | − | + | − | − | − |
| 8) Saccharose | + | − | + | − | − | − |
| 9) Lactose | + | − | − | − | − | − |

A-2 Physiological characteristics of gram-positive, spore-forming bacilli

| Characteristics | Strain NRS-85KH20B (FERM-P No. 3164) (NRRL B-11084) | | NRS-112KH25B (FERM-P) No. 3165) NRRL 11085) | | NRS-137KH20B (FERM-P) No. 3169) (ATCC 31301) | |
|---|---|---|---|---|---|---|
| 10) Trehalose | + | − | + | − | − | − |
| 11) D-sorbitol | − | − | − | − | − | − |
| 12) D-mannitol | + | − | − | − | − | − |
| 13) Inositol | (+) | − | + | − | (−) | − |
| 14) Glycerine | + | − | + | − | (−) | − |
| 15) Starch | + | − | + | − | − | − |
| 18 Caseine hydrolysis | + | | + | | + | |
| 19 Tyrosine hydrolysis | / | | / | | + | |
| 20 Phenylalanine deaminase | / | | / | | + | |
| Source of soil sample | Nerima-ku, Tokyo, Japan | | Tobata-ku, Kita-Kyushu-shi, Japan | | Kiyosato, Nagano Pref., Japan | |

B-1) Morphological characteristics and culture characteristics of pleomorphic bacteria

| Characteristics | Strain NRS-112KH31B (FERM-P No. 3166) (NRRL B-11086) | NRS-129KH5B2 (FERM-P No. 3167) (ATCC 31300) | NRS-130-KH-20B (FERM-P No. 3657) (NRRL B-11088) | NRS-135KH9B (FERM-P. No. 3168) (NRRL B-11087) |
|---|---|---|---|---|
| a) Morphology | | | | |
| 1 Pleomorphism | + | + | + | + |
| 2 Form | bacilli Acid-fast bacilli become coccoid cells | bacilli become coccoid cells | bacilli become coccoid cells | coccoid cells |
| 3 Size (μ) 24 hrs. | 0.5–1.0 × 3.0–5.0 | 0.5–1.0 × 3.0–5.0 | 0.5–1.0 × 3.0–5.0 | 1.2–1.5 × 2.5–6.0 |
| 48 hrs. | 0.5–0.8 × 1.0–1.5 | 0.5–0.8 × 1.0–1.5 | 0.5–0.8 × 1.0–1.5 | 0.5–1.0 × 1.0–1.5 |
| 4 Motility | − | − | − | − |
| 5 gram straining | + | + | + | + |
| 6 Acdi-fast staining colouring | − | − | − | − |
| 7 Spores | − | − | − | − |
| b) Characteristics of the culture | | | | |
| 1 Nutrient agar plate | | | | |
| Form | convex, entirely smooth | convex, entirely smooth | convex, entirely smooth | convex, entirely smooth |
| Opacity | translucent | translucent | translucent | opaque |
| Colour of the colony | cream | cream | cream-white | cream |
| Soluble pigment | none | none | none | none |
| 2 Nutrient agar slant | | | | |
| Growth | abundant | abundant | abundant | abundant |
| Form | filiform | filiform | filiform | filiform |
| Lustre | glistening | glistening | glistening | glistening |
| Colour of the colony | cream-white | cream-white | cream-white | cream-white |
| Soluble pigment | none | none | none | none |
| 3 Bouillon liquid | | | | |
| Growth | moderate | moderate | moderate | abundant |
| Surface growth | none | none | none | abundant |
| Precipitate | scant | scant | scant | moderate |
| Pigmentation | none | none | none | none |
| 4 Gelatine stab culture | | | | |
| Growth | moderate to abundant | moderate to abundant | moderate to abundant | moderate |
| Liquefaction | + | + | + | − |
| 5 Litmus milk | | | | |
| Litmus | alkaline | alkaline | alkaline | alkaline |
| Peptonisation | − | − | − | − |
| Coagulation | − | − | − | − |

| | B-2) Physiological characteristics of pleomorphic bacteria. | | | |
|---|---|---|---|---|
| Characteristics | Strain NRS-112KH31B (FERM-P No. 3166) (NRRL B-11086) | NRS-129KH5B2 (FERM-P NO. 3167) (ATCC 31300) | NRS-130KH20B (FERM-P No. 3657) (NRRL B-11088) | NRS-135KH9B (FERM-P No. 3168) (NRRL B-11087) |
| c) Physiological characteristics | | | | |
| 1 Nitrate reduction | − | − | − | − |
| 2 Nitrate respiration | − | − | − | − |
| 3 MR-test | − | − | − | − |
| 4 VP-test | − | − | − | − |
| 5 Indole production | − | − | − | − |
| 6 H$_2$S-production | − | − | − | − |
| 7 Starch hydrolysis | − | − | − | − |
| 8 Citrate utilisation | | | | |
| a. Koser medium | + | + | + | + |
| b. Christensen medium | + | + | + | + |
| 9 Utilisation of | | | | |
| NaNO$_3$ | + | + | + | + |
| (NH$_4$)$_2$SO$_4$ | + | + | + | + |
| Urea | + | + | + | + |
| Na glutamate | + | + | + | + |
| 10 Pigment formation | − | − | − | − |
| 11 Urease | − | − | (−) | + |
| 12 Oxidase | − | − | − | − |
| 13 Catalase | + | + | + | + |
| 14 Growth range pH | 5.0–9.5 | 5.0–9.0 | 5.0–10.0 | 5.0–10.0 |
| Temperaure | 15° C.–37° C. | 10° C.–37° C. | 10° C.–37° C. | 5° C.–30° C. |
| 15 Aerobic growth | + | + | + | + |
| Anaerobic growth | + | + | + | + |
| 16 O-F test | (fermentation) | (fermentation) | (fermentation) | (fermentation) |
| 17 Acid and gas | acid / gas | acid / gas | acid / gas | acid / gas |
| 1) L-arabinose | − / − | − / − | − / − | − / − |
| 2) D-xylose | + / − | (+) / − | (+) / − | (+) / − |
| 3) D-glucose | + / − | + / − | (+) / − | + / − |
| 4) D-mannose | − / − | − / − | (+) / − | − / − |
| 5) D-fructose | + / − | + / − | (+) / − | + / − |
| 6) D-galactose | + / − | (+) / − | − / − | − / − |
| 7) Maltose | − / − | − / − | (+) / − | − / − |
| 8) Saccharose | − / − | − / − | (+) / − | + / − |
| 9) Lactose | − / − | − / − | − / − | − / − |
| 10) Trehalose | + / − | (+) / − | − / − | + / − |
| 11) D-sorbitol | + / − | + / − | − / − | + / − |
| 12) D-mannitol | − / − | − / − | − / − | + / − |
| 13) Inositol | − / − | (+) / − | (+) / − | (+) / − |
| 14) Glycerine | − / − | + / − | (+) / − | + / − |
| 15) Starch | − / − | − / − | − / − | − / − |
| 18 Casein hydrolysis | − | − | + | − |
| 19 DN-ase | − | − | + | − |
| 20 Growth in 5% NaCl | + | + | + | + |
| 21 Growth in 10 NaCl | − | − | − | − |
| Source of soil sample | Tobata-ku, Kitakyushu, Japan | Shinano-Ohmachi Nagano-Pref., Japan | Fuji-shi, Shizuoka-Pref., Japan | Shosenkyo, Yamanashi-Pref., Japan |

| | C-1) Morphological characteristics and characteristics of the culture of gram-negative bacilli. | | | |
|---|---|---|---|---|
| Characteristics | Strain NRS-137CzH5B (FERM-P No. 3658) (NRRL 11089) | NRS-146KH6B (FERM-P No. 3172) (ATCC 31303) | NRS-140KH27B (FERM-P No. 3659) (NRRL 11090) | NRS-139KH6B (FERM-P No. 3170) (ATCC 31302) |
| a) Morphology | | | | |
| 1 Form | bacilli | bacilli | bacilli | bacilli |
| 2 Size (μ) | 0.4–0.6 × 1.5–2.5 | 0.5–0.8 × 1.5–3.0 | 0.5–0.8 × 2.0–3.5 | 0.4–0.7 × 1.0–1.5 |
| 3 Pleomorphism | | − | − | − |
| 4 Motility | + | + | + | + |
| 5 Spores | − | − | − | − |
| 6 gram staining | − | − | − | − |
| 7 Acid-fast staining colouring | − | − | − | − |
| b) Characteristics of the culture | | | | |
| 1 Nutrient agar | | | | |

-continued

| | C-1) Morphological characteristics and characteristics of the culture of gram-negative bacilli. | | | |
|---|---|---|---|---|
| Strain<br>Characteristics | NRS-137CzH5B<br>(FERM-P No. 3658)<br>(NRRL 11089) | NRS-146KH6B<br>(FERM-P No. 3172)<br>(ATCC 31303) | NRS-140KH27B<br>(FERM-P No. 3659)<br>(NRRL 11090) | NRS-139KH6B<br>(FERM-P No. 3170)<br>(ATCC 31302) |
| plate | | | | |
| Form | convex, entirely smooth | umbonate, entirely wrinkled | convex, entirely wrinkled | convex, entirely smooth |
| Opacity | translucent | translucent | translucent | opaque |
| Colour of the colony | pale yellow to orange | pale yellow to orange | pale yellow | cream-white |
| Soluble pigment | none | none | none | none |
| 2 Nutrient agar slant | | | | |
| Growth | abundant | abundant | abundant | moderate |
| Form | filiform | filiform | filiform | filiform |
| Lustre | glistening | glistening | glistening | glistening |
| Colour of the colony | pale brown to orange | pale brown to orange | pale brown | cream-white |
| Soluble pigment | none | none | none | none |
| 3 Bouillon liquid | | | | |
| Growth | abundant | abundant | abundant | moderate |
| Surface growth | slight | abundant | abundant | abundate |
| Precipitate | moderate | slight | moderate | slight |
| Pigmentation | faint yellowish | faint yellowish | none | none |
| 4 Gelatine stab culture | | | | |
| Growth | moderate to abundant | moderate | moderate | moderate |
| Liquefaction | + | − | − | − |
| 5 Litmus milk | | | | |
| Litmus | alkaline | alkaline | alkaline | alkaline |
| Peptonisation | + | − | − | − |
| Coagulation | − | − | − | − |

| | C-2) Physiological characteristics of gram-negative bacilli | | | |
|---|---|---|---|---|
| Strain<br>Characteristics | NRS-137CzH5B<br>(FERM-P No. 3658)<br>(NRRL 11089) | NRS-146KH6B<br>(FERM-P No. 3172)<br>(ATCC 31303) | NRS-140KH27B<br>(FERM-P No. 3649)<br>(NRRL 11090) | NRS-139KH6B<br>(FERM-P No. 3170)<br>(ATCC 31302) |
| c) Physiological characteristics | | | | |
| 1 Nitrate reduction | − | + | − | − |
| 2 Nitrate respiration | − | − | − | − |
| 3 MR-test | − | − | − | − |
| 4 VP-test | − | − | − | − |
| 5 Indole production | − | − | − | − |
| 6 H$_2$S-production | − | − | − | − |
| 7 Starch hydrolysis | − | − | − | − |
| 8 Citrate utilisation | | | | |
| a. Koser medium | + | + | + | + |
| b. Christensen medium | + | + | + | + |
| 9 Utilisation of | | | | |
| NaNO$_3$ | + | + | + | + |
| (NH$_4$)$_2$SO$_4$ | + | + | + | + |
| Urea | + | + | + | + |
| Na-glutamate | + | + | + | + |
| 10 Pigment formation | fluorescing soluble | fluorescing soluble | fluorescing soluble | none |
| 11 Urease | − | − | − | + |
| 12 Oxidase | + | + | + | + |
| 13 Catalase | + | + | + | + |
| 14 Growth range | | | | |
| pH | 5.0–10.0 | 5.0–10.0 | 5.0–9.0 | 5.0–9.5 |
| Temperature | 5° C.–30° C. | 5° C.–37° C. | 5° C.–37° C. | 20° C.–30° C. |
| 15 Aerobic Growth | + | + | + | + |
| Anaerobic Growth | + | + | + | + |
| 16 O-F test | oxidation | oxidation | oxidation | oxidation |
| 17 Acid and gas | acid   gas | acid   gas | acid   gas | acid   gas |
| 1) L-arabinose | +   − | +   − | +   − | +   − |
| 2) D-xylose | +   − | +−   +− | +−     |     |
| 3) D-glucose | +   − | +   − | +−   +− |     |
| 4) D-mannose | +   − | +   − | +   − | +   − |
| 5) D-fructose | (−)   − | +   − | +   − | +   − |
| 6) D-galactose | +   − | +   − | +   − | +   − |

| | C-2) Physiological characteristics of gram-negative bacilli | | | |
|---|---|---|---|---|
| Characteristics | Strain NRS-137CzH5B (FERM-P No. 3658) (NRRL 11089) | NRS-146KH6B (FERM-P No. 3172) (ATCC 31303) | NRS-140KH27B (FERM-P No. 3649) (NRRL 11090) | NRS-139KH6B (FERM-P No. 3170) (ATCC 31302) |
| 7) Maltose | − | − | − | + |
| 8) Saccharose | − | − | (−) | + |
| 9) Lactose | (−) | − | − | + |
| 10) Trehalose | − | − | (−) | + |
| 11) D-sorbitol | (+) | − | (−) | + |
| 12) D-mannitol | (+) | − | (−) | + |
| 13) Inositol | (+) | − | (−) | + |
| 14) Glycerine | (+) | + | + | + |
| 15) Starch | − | − | − | − |
| 18 Casein hydrolysis | + | − | − | − |
| 19 Arginine hydrolysis | + | + | + | − |
| Source of the soil sample | Kiyosato, Nagano Pref., Japan | Sarugakyo, Gumma Pref., Japan | Shimada-shi Shizuoka Pref., Japan | Kiyosato, Nagano Pref., Japan |

From the foregoing it is evident that these strains can be identified as follows based on Bergey's Manual of Determinative Bacteriology (8th Ed., 1974; 7th Ed., 1957); Riichi Sakazaki, "Identification of Medical Bacteria," Kindai Shuppan, 1971; and Kazuhiko Yamada and Kazuo Komagata., J. Gen. Appl. Microbiol., 18, 417, 1972:

(1) Strain FERM-P No. 3164 (NRRL B-11084):

An acid-forming variant of Bacillus megaterium anaerobically from glucose.

(2) Strain FERM-P No. 3165 (NRRL 11085):

Bacillus species, having certain similarities with B. circulans and B. firmus. However, the strain differs from the first strain by the morphology of the spores and from the latter strain by the anaerobic growth.

(3) Strain FERM-P No. 3169 (ATCC 31301):

Identified as Bacillus freudenreichii.

(4) Strain FERM-P No. 3166 (NRRL B-11086), FERM-P No. 3167 (ATCC 31300), FERM-P No. 3657 (NRRL B-11088) and FERM-P No. 3168 (NRRL 11087):

These four strains are aerobic to facultative anaerobic, gram-positive, non-motile, non-spore forming and non-acid fast, straight to slightly curved bacilli in the first growth phase and spherical to ovoid after more than 1 days growth. These characteristics show that all of these strains belong to the so-called Coryne-form group. It is known to be difficult to suggest the family and genus for this group (see e.g. Yamada, Komagata, J. Gen. Appl. Microbiol., 18, 417, 1972). However, the following identification is possible on the basis of Bergey's Manual. The various genera of the Coryne-form group all differ from the genus Arthrobacter by the acid production on glucose, fructose and other sugars, from the genus Kuruthia by the absence of motility, from the genus Microbacterium in that all these strains do not survive upon heating in skimmed milk to 72° C. for 15 minutes, and from the genus Cellulomonas by the inability to utilise cellulose.

Strain FERM-P No. 3168 (NRRL B-11087):

From the characteristics given in the Tables it is evident that this strain is very closely related to Corynebacterium callunae, Brevibacterium lactofermentum, B. vitaruman and C. hydrocarboclastus. The three latter strains differ, however, from strain No. 3168 by their pleomorphic characteristics and by granula formation. In spite of the differences in the utilisation of sugars and in the acid production, strain FERM-P No. 3168 (NRRL B-11087) is related closest to C- hydrocarboclastus and has therefore been identified as a variant of C. hydrocarboclastus.

Strain FERM-P No. 3657 (NRRL B-11088):

The characteristics of this strain, namely the absence of the formation of granula, acid production, hydrolytic activities towards gelatine and casein, positive DN-ase, negative urease and absence of growth in 10% sodium chloride leads to the conclusion that the strain No. 3657 is very closely related to Brevibacterium albidum. In spite of some difference in the acid production on D-mannose, saccharose, inositol and glycerin, strain FERM-P No. 3657 (NRRL B-11088) has been identified as B. albidum on the basis of the analogy between all other characteristics.

Strain FERM-P No. 3166 (NRRL B-11086) and FERM-P No. 3167 (ATCC 31300):

These two strains are very similar and are not distinguishable from one another. Under the types described in Bergey's Manual (7th and 8th Ed.) and Komagata et al. (J. Gen. Appl. Microbiol., 18, 399, 1972) Brevibacterium tegmenticola was found to be related the closest. Since, however, these strains differ from B. tegmenticola by the size of the cells, the reactions in litmus milk and the acid production on maltose and saccharose, identity can not be said to exist. It therefore appears convenient to regard these strains as novel types which have a certain similarity to B. tegmenticola.

(5) Strain FERM-P No. 3658 (NRRL 11089):

Identified as Pseudomonas fluorescens.

(6) Strains FERM-P No. 3172 (ATCC 31303) and FERM-P No. 3659 (NRRL 11090):

Identified as *Pseudomonas putida*. Some differences between the characteristics of the two strains such as, for example, the nitrate reduction, were established. Since it could be established that the nitrate reduction was positive with strains of this type, strain FERM-P No. 3659 (NRRL 11090) can be regarded as being a nitrate non-reducing variant of *Ps. putida*.

(7) Strain FERM-P No. 3170 (ATCC 31302):

Pseudomonas species. Among various Pseudomonas strains, strain FERM-P No. 3170 (ATCC 31302) is related closest to *Ps. cepacia*. On the basis of the differences in gelatine liquefaction, casein hydrolysis, growth at 42° C. and nitrate reduction, the strain can not be regarded as being identical with *Ps. cepacia*.

The isolated actinomycetes have the following growth characteristics:

(1) Strain FERM-P No. 3160 (NRS-79KH-1A, NRRL 11083):

This strain, isolated from a soil sample from Uwajima-shi, Ehime Pref., Japan, develops well on various ISP-agar media for actinomycetes and forms a well-developed aerial mycelium with spore-forming hyphae. The spores, which appear in the form of chains of about 50 spores per chain, are cylindrical, have a spiny surface and a size of $0.4 \sim 0.8 \times 0.8 \sim 1.4 \mu$. The formation of other specific organs was not observed.

On most of the tested agar media the growth (vegetative mycelium) is light brownish-grey to pale brown and the aerial mycelium is light grey to grey. The soluble pigment is brownish to reddish. The formation of melanin-like pigment was not observed.

(2) FERM-P No. 3660 (NRS-125KH-27A, NRRL 11091):

This strain, isolated from a soil sample from Suwa-shi, Nagano Pref., Japan, also develops well on various ISP-agar media. A relatively long, straight or flexuous aerial mycelium forms from a well developed vegetative mycelium. Neither whirl nor spiral formations are observed. The spores, in chains of more than 50 spores per chain, are cylindrical, have a smooth surface and a size of $0.5-0.7 \times 0.8-1.2\mu$.

The growth is weak yellowish-brown to weak yellow and the aerial mycelium is white. A yellowish soluble pigment forms. No melanin-like pigment was observed.

From the foregoing characteristics it is clearly evident that strains FERM-P No. 3160 (NRRL 11083) and FERM-P No. 3660 (NRRL 11091) are typical Streptomyces species.

The asymmetric dehydrogenation in accordance with the present invention can be carried out, for example, by contacting the culture broth or cultivated cells of the microorganisms with a DL-α-hydroxycarboxylic acid of formula I or a salt thereof. The culture broth can be prepared by inoculating a suitable medium with the microorganism. The culture medium can contain, for example, meat extract, yeast extract, peptone, cornsteep liquor, other natural substances usually used or mixtures thereof, as well as saccharides or other carbon sources, or organic or inorganic, nitrogen-containing compounds such as amino acids or nitric acid. If necessary, the pH of the culture medium can be adjusted to 7 by the addition of suitable salts such as a sodium phosphate or sodium chloride or another metal salt. Submerged cultures, shaking cultures or stationary cultures can be used. The cultivation is, however, preferably carried out under aerobic conditions. The temperature at which the cultivation is carried out generally lies in the range of 20°-40° C., preferably in the range of 25°-35° C. The cultivation is conveniently carried out for 20-80 hours. Under the cultivation conditions described earlier the growth of the strain attains the stationary phase. A DL-α-hydroxycarboxylic acid of general formula I or a salt thereof can be added as the substrate to the culture broth in which the growth of the strain has attained the stationary phase. The concentration of the substrate is conveniently 1-200 mg/ml, preferably 3-120 mg/ml. The asymmetric dehydrogenation can be carried out under the conditions described earlier by continuing the submersed culture, the shaking culture or the stationary culture. The time required for the asymmetric dehydrogenation depends, inter alia, on the species and the strain of the microorganism used, the composition of the medium, the nature and the concentration of the substrate. In general, however, a time of 70-360 hours is sufficient. The end of the asymmetric dehydrogenation can be determined by measuring the amount of asymmetric dehydrogenation product by gas-chromatographic or colorimetric methods, as further described hereinafter.

The asymmetric dehydrogenation can also be carried out under the conditions described earlier by adding the substrate to the culture medium and subsequently inoculating with the microorganism.

Further, the asymmetric dehydrogenation can be carried out by contacting treated cell substance with a DL-α-hydroxycarboxylic acid of formula I or a salt thereof. The term "treated cell substance" used herein denotes all materials which have been obtained by treatment of the microorganisms and which are capable of continuing or increasing the enantiospecific dehydrogenase activity. Such materials are, for example, the mycelium or cells, which have been isolated from the culture broth and washed, or lyophilised powder therefrom; cell-free extract obtained in a manner known per se from the cultivated cells or from the mycelium; or purified or partially purified dehydrogenase preparations which have been obtained in a manner known per se by purification from the aforementioned cell-free extracts. Where such a treated cell substance is used, the asymmetric dehydrogenation can be carried out in an aqueous solution, for example a buffer solution or a fresh medium. The pH of the solution usually lies between 7 and 8.5, especially at about 8. The temperature conveniently lies at 20°-60° C., especially at 25°-50° C. The completion of this asymmetric dehydrogenation can be determined by measuring the amount and the optical purity of the residual α-hydroxycarboxylic acid as well as the amount of the ketocarboxylic acid formed in the culture broth or the mixture by gas-chromatographic or colorimetric methods.

By the asymmetric dehydrogenation in accordance with the invention one of the enantiomers of the DL-α-hydroxycarboxylic acid of formula I or a salt thereof is selectively converted into the corresponding α-ketocarboxylic acid or a salt thereof, while the other enantiomer remains behind in the form of the optically active α-hydroxycarboxylic acid or a salt thereof. Whether the remaining optically active substance is present in D- or L-form depends on the nature of the microorganism used.

When the D-form is desired, the following microorganisms can be used:

| | |
|---|---|
| *Bacillus megaterium* | (FERM-P No. 3164, NRRL B-11084) |
| Bacillus sp. | (FERM-P No. 3165, NRRL 11085) |
| *Pseudomonas fluorescens* | (FERM-P No. 3658, NRRL 11089) |
| Brevibacterium sp. related to *B. tegmenticola* | (FERM-P No. 3166, NRRL B-11086 and FERM-P 3167, ATCC 31300) |
| *Brevibacterium albidum* | (FERM-P No. 3657, NRRL B-11088) |
| Streptomyces sp. | (FERM-P No. 3160, NRRL 11083) |

When the L-form is desired, the following microorganisms can be used:

| | |
|---|---|
| *Bacillus freudenreichii* | (FERM-P NO. 3169, ATCC 31301) |
| *Pseudomonas putida* | (FERM-P NO. 3172, ATCC 31303 and FERM-P 3659, NRRL 11090) |
| Pseudomonas sp. | (FERM-P No. 3170, ATCC 31302) |
| Corynebacterium hydrocarboclastus var. | (FERM-P NO. 3168, NRRL B-11087) |

| | |
|---|---|
| Streptomyces sp. | (FERM-P NO. 3660, NRRL 11091). |

Where the products of the asymmetric dehydrogenation are obtained in the form of salts, the latter can be converted by addition of an acid into the free optically active α-hydroxycarboxylic acids and α-ketocarboxylic acids.

The optically active α-hydroxycarboxylic acids and the α-ketocarboxylic acids can be isolated from the solution in a manner known per se; for example, on the basis of solubility differences, by chromatographic fractionation using an ion exchange resin or silica gel or by fractional distillation. The compounds can also be treated with hydrazines in a manner known per se, the α-ketocarboxylic acids being converted selectively into the hydrazones which can be separated by usual fractionation methods.

According to the process provided by the present invention optically pure D- or L-α-hydroxycarboxylic acids and α-ketocarboxylic acids are manufactured in high yield and in a simple manner.

In a preferred embodiment of the process provided by the present invention, the resulting α-ketocarboxylic acid is hydrogenated in a manner known per se and the hydrogenation product is recycled into the asymmetric dehydrogenation as the starting material. The hydrogenation can be carried out in a manner known per se, preferably in the presence of a catalyst such as Raney-nickel. Where water is used as the solvent in the catalytic hydrogenation, the catalyst is filtered off, the filtrate is concentrated and the concentrate can then be used directly for the asymmetric dehydrogenation.

The α-hydroxycarboxylic acids obtained according to the present process can be used as intermediates for the manufacture of pharmaceutical products; for example penicillins (see U.S. Pat. No. 3,839,322 and the reissue thereof U.S. Pat. No. Re. 29,003 as well as U.S. Pat. Nos. 3,956,323 and 3,957,758), amino acids and the like, as well as biochemical reagents. Important representatives of the aforementioned α-hydroxycarboxylic acids and D- and L-lactic acid.

The following Examples illustrate the present invention:

The media used in the Examples are aqueous media having the following composition:

| Medium A (pH 7.0) | |
|---|---|
| Glucose | 0.1% |
| Peptone | 1.0% |
| Meat extract | 0.3% |
| Sodium chloride | 0.5% |
| Medium B (pH 7.0) | |
| Glucose | 0.1% |
| Cornsteep liquor | 2.0% |

In the Examples, the given amount of α-hydroxycarboxylic acid remaining, its optical purity and the amount of α-ketocarboxylic acid obtained can be determined by the following methods.

(1) Quantitative determination of the alpha-hydroxycarboxylic acids in the fermentation broths:

2.0 ml of fermentation broth filtrate are taken up in a 10 ml centrifuge tube containing 1.6 g of ammonium sulphate, acidified with 10% sulphuric acid and then extracted with 2.0 ml of ethyl acetate. 1.5 ml of the ethyl acetate extract are evaporated under reduced pressure. 2 ml of toluene are added to the residue and the mixture is again evaporated to dryness. The residue is dissolved in 0.2 ml of pyridine and 0.1 ml of benzoyl chloride are added. After 20 minutes at room temperature, the mixture is cooled in an ice-bath, treated with 1.0 ml of a 5:1 mixture of toluene and n-propanol containing 0.4% diethyl terephthalate (internal standard, I.S.) and left at room temperature for 20 minutes. After the addition of 2.0 ml of water, the mixture is shaken and then centrifuged for 5 minutes at 3000 revolutions per minute. The toluene layer is dried over anhydrous sodium sulphate and a part of the solution (usually 2 μl) is analysed by gas chromatography under the folloing conditions:

| | |
|---|---|
| Temperature: | Column 185° C., Injector 225° C., Detector 205° C. |
| Column: | Long glass Length 2 m Internal diameter 3 mm |
| Column packing: | 5% QF-1/chromosolve W, MMCS 80–900 mesh |
| Carrier gas: | 30 ml/minute helium |
| Detection: | FID |

The retention times of the I.S. and the derivatives of the α-hydroxycarboxylic acids, e.g. α-hydroxy-γ-methylvaleric acid and α-hydroxyhexanoic acid, are 4.4, 6.6 and 7.8 minutes, respectively, under the foregoing conditions. The areas corresponding to the peaks are converted into concentration values by means of a calibration curve.

(2) Determination of the optical purity of the α-hydroxycarboxylic acids in fermentation broths:

7 ml of the fermentation broth filtrate are acidified with 1 ml of 10% sulphuric acid and extracted with 5 ml of ethyl acetate. 4 ml portions of the ethyl acetate extract are evaporated to dryness under reduced pressure. The residue is treated with 2 ml of n-propanol containing 4% hydrogen chloride. After 3 hours at room temperature, the mixture is evaporated under reduced pressure and the last traces of n-propanol are removed by means of toluene. 0.2 ml of L-(—)-menthyloxycarbonyl chloride solution (prepared according to the method of J. W. Westley, J. Org. Chem. 33, 3798, 1968) and 0.2 ml of pyridine are added to the residue. After 30 minutes at room temperature, the mixture is treated with 2 ml of cold water. Then, 0.8 ml of toluene is added. The mixture is shaken and centrifuged. After drying over sodium sulphate, a part of the toluene phase is analysed by gas chromatography under the same conditions as described earlier for the quantitative determination of the α-hydroxycarboxylic acids. Examples of retention times for some diastereomeric carbonates derived from α-hydroxycarboxylic acids are given in the following Table. The optical purity can be ascertained by means of the following equation:

AL: Area of the peak of the L-enantiomer
AD: Area of the peak of the D-enantiomer/k
k: Ratio of detector response to the diastereomers (LD/LL)

$$\text{Optical purity} = \frac{|AL - AD|}{AL + AD} \times 100\ (\%)$$

| R in formula I | Retention time of the L-enantiomer in minutes | Retention time of the D-enantiomer in minutes | k |
|---|---|---|---|
| $CH_3(CH_2)_2$ | 8.5 | 9.2 | 0.96 |

-continued $$\text{Optical purity} = \frac{|AL - AD|}{AL + AD} \times 100 \, (\%)$$

| R in formula I | Retention time of the L-enantiomer in minutes | Retention time of the D-enantiomer in minutes | k |
|---|---|---|---|
| (CH$_3$)$_2$CHCH$_2$ | 8.8 | 9.6 | 1.00 |
| CH$_3$(CH$_2$)$_3$ | 10.8 | 11.8 | 1.16 |
| CH$_3$(CH$_2$)$_4$ | 14.0 | 15.3 | 1.14 |
| CH$_3$(CH$_2$)$_5$ | 18.4 | 20.2 | 1.17 |
| CH$_3$(CH$_2$)$_6$ | 24.5 | 26.7 | 1.15 |
| CH$_3$(CH$_2$)$_7$ | 32.4 | 35.3 | 1.05 |
| CH$_3$(CH$_2$)$_9$ | 57.8 | 63.0 | 1.00 |

(3) Quantitative determination of the α-ketocarboxylic acids:

The colorimetric method of H. Katsuki et al., Anal. Biochem. 43, 349 (1971) is used.

The following Examples illustrate the invention

EXAMPLE 1

Four 500 ml Erlenmeyer flasks provided with a baffle were treated in an autoclave with in each case 100 ml of medium A and then inoculated with Bacillus sp. NRS-112KH25B (FERM-P No. 3165, NRRL 11085) from a slant culture. The incubation was carried out for 26 hours at 27° C. while shaking (180 movements per minute). Thereafter, 3.54 g of sodium DL-2-hydroxy-4-methylvalerate were added to each flask and the fermentation was continued for 84 hours at 27° C. while shaking. By means of the gas chromatographic method described earlier it was found that the substrate remaining in the culture broth contained 15.5 mg/ml of free D-hydroxyacid (optical purity: 100%).

The thus-obtained fermentation broth (390 ml) was acidified with 50 ml of 20% sulphuric acid and extracted with 300 ml of ethyl acetate. The aqueous layers were again extracted with 100 ml of ethyl acetate. The combined ethyl acetate extracts were dried over anhydrous sodium sulphate and concentrated under reduced pressure. After recrystallization of the residue from diethyl ether/petroleum ether, there were obtained 4.95 g of D-2-hydroxy-4-methylvaleric acid of melting point 79.6° C.; $[\alpha]_D^{25} = +26.3°$ (c=2 in 1-N sodium hydroxide); empirical formula: C$_6$H$_{12}$O$_3$ ascertained by mass spectrometry with high resolution.

The mother liquor was concentrated under reduced pressure and the yellowish-brown oily residue was subjected to fractional distillation, there being obtained 3.6 g of 4-methyl-2-oxovaleric acid in the form of a colourless oil of boiling point 65°–75° C./10 mmHg; empirical formula: C$_6$H$_{10}$O$_3$ ascertained by mass spectrometry with high resolution.

EXAMPLE 2

A 500 ml Erlenmeyer flask provided with a baffle and containing 90 ml of medium A was inoculated with Bacillus freudenreichii NRS-137KH20B (FERM-P No. 3169, ATCC 31301) from a slant culture. The incubation was carried out for 24 hours under the conditions described in Example 1. Thereafter, 3.17 g of sodium DL-2-hydroxy-4-methylvalerate were added and the fermentation was continued for 82 hours. The substrate remaining in the fermentation broth contained 15.2 mg/ml of free L-hydroxyacid (optical purity: 100%). The thus-obtained fermentation broth was then treated in an analogous manner to that described in Example 1 and there were obtained 1.18 g of crystalline L-2-hydroxy-4-methylvaleric acid of melting point 79.1° C. [$[\alpha]_D^{25} = -26.8°$ (c=2 in 1-N sodium hydroxide)] and 0.7 g of 4-methyl-2-oxovaleric acid of boiling point 65°–75° C./10 mmHg.

EXAMPLE 3

Ten 500 ml Erlenmeyer flasks provided with a baffle and containing in each case 100 ml of medium B were inoculated with Coryneform strain NRS-130KH20B (FERM-P No. 3657, NRRL B-11088) from a slant culture and incubated for 24 hours under the same conditions as described in Example 1. 8.19 g of sodium DL-2-hydroxy-4-methylvalerate were added to each flask as the substrate and the fermentation was continued for 120 hours under the same conditions. According to the method described earlier it was found that 120 hours after the addition of the substrate 35 mg/ml of 4-methyl-2-oxovaleric acid and 37mg/ml of pure D-hydroxy-acid were present. The fermentation was therefore discontinued and the fermentation broth were combined and centrifuged. The supernatant was acidified to pH 1.5 with 38 ml of 50% sulphuric acid and extracted three times with 1 liter of diethyl ether. The combined ether extracts were washed three times with 10 ml of saturated sodium chloride solution and evaporated under reduced pressure. 100 ml of toluene were added to the residue and the mixture was concentrated under reduced pressure in order to remove the water. The yellowish-brown oily residue was dissolved in 400 ml of petroleum ether and the solution was stored overnight in the refrigerator. The crystallisate was collected by filtration, washed with 50 ml of cold petroleum ether and dried in vacuo. There were obtained 28.1 g of D-2-hydroxy-4-methylvaleric acid in the form of colourless crystals of melting point 79.9° C.; $[\alpha]_D^{20} = +26.67°$ (c=2 in 1-N sodium hydroxide).

EXAMPLE 4

The mother liquor and wash-water from Example 3, containing 4-methyl-2-oxovaleric acid and a small amount of D-2-hydroxy-4-methylvaleric acid, were combined and transferred to a separating funnel. Then, 1-N sodium hydroxide was added while shaking until the pH of the aqueous layer was 7.0 (addition of 299 ml of 1-N sodium hydroxide). The aqueous layer was separated and concentrated to about 150 ml under reduced pressure. To the residue were added 100 ml of distilled water containing Raney-nickel T4 (prepared from 36 g of a nickel/aluminum alloy containing 42% nickel according to the method of Nishimura, Bull. Chem. Soc. Japan, 32, 61–64, 1959). The mixture was hydrogenated at room temperature under normal pressure until the uptake of hydrogen ceased. The catalyst was filtered off. The filtrate was acidified with 25 ml of 50% sulphuric acid and then extracted four times with 500 ml of diethyl ether. The ether extracts were combined, washed with 10 ml of saturated sodium chloride solution and concentrated under reduced pressure. 100 ml of toluene were added to the residue and the mixture was again concentrated under reduced pressure to a light yellow oil. 160 ml of petroleum ether were added to bring about crystallisation. The mixture was stored overnight in a refrigerator, filtered and the crystals were washed with cold petroleum ether, there being obtained 32.3 g of 2-hydroxy-4-methylvaleric acid in the form of colourless crystals of melting point 73.9° C.; $[\alpha]_D^{20} = +4.24°$ (c=2 in 1-N sodium hydroxide).

EXAMPLE 5

DL-2-Hydroxy-4-methylvaleric acid was dissolved in medium A up to a concentration of 3.0 mg/ml and the pH was adjusted to 7.0 by the addition of 5-N sodium hydroxide. Three 500 ml Erlenmeyer flasks containing in each case 100 ml of the thus-prepared medium were sterilised in an autoclave and then inoculated with one of the following strains: Bacillus megaterium NRS-85KH20B (FERM-P No. 3164, NRRL B-11084), Pseudomonas fluorescens NRS-137CzH5B (FERM-P No. 3658, NRRL 11089) and Streptomyces sp. NRS79KH1A (FERM-P No. 3160, NRRL 11083). The cultivation was carried out at 27° C. while shaking (180 movements/minute). After 72 and 144 hours, the fermentation broth was analysed gas chromatographically as described earlier. The following results were obtained.

| Strain | Amount of substrate remaining (optical purity as the D-enantiomer) | | | | |
|---|---|---|---|---|---|
| | 0 hours (beginning of the cultivation) | | 72 hours | | 144 hours |
| FERM-P No. 3164, NRRL B-11084 | 3.0 mg/ml | (0%) | 1.9 mg/ml | ( 76%) | 1.8 mg/ml ( 92%) |
| FERM-P No. 3658, NRRL 11089 | 3.0 | (0%) | 1.2 | (100%) | 1.1 (100%) |
| FERM-P No. 3160, NRRL 11083 | 3.0 | (0%) | 1.2 | (100%) | 1.2 (100%) |

EXAMPLE 6

The following strains in medium A containing 3.0 mg/ml of DL-2-hydroxy-4-methylvaleric acid were cultivated according to the method described in Example 5: Bacillus freudenreichii NRS-137KH20B (FERM-P No. 3169, ATCC 31301), Pseudomonas putida NRS-146KH6B (FERM-P No. 3172, ATCC 31303), Pseudomonas sp. NRS-139KH6B (FERM-P No. 3170, ATCC 31302), Coryneform NRS-135KH9B (FERM-P No. 3168, NRRL B-11087) and Streptomyces sp. NRS-125KH27A (FERM-P No. 3660, NRRL 11091). The fermentation broth was analysed by the method described earlier after 72 and 144 hours. The results are given in the following Table:

| Strain | Amount of substrate remaining (optical purity as the L-enantiomer) | | | | |
|---|---|---|---|---|---|
| | 0 hours (beginning of the cultivation) | | 72 hours | | 144 hours |
| FERM-P No. 3169, ATCC 31301 | 3.0 mg/ml | (0%) | 1.6 mg/ml | (93%) | 1.4 mg/ml (100%) |
| FERM-P No. 3172, ATCC 31303 | 3.0 | (0%) | 1.4 | (98%) | 1.4 (100%) |
| FERM-P No. 3170, ATCC 31302 | 3.0 | (0%) | 1.3 | (93%) | 1.0 (100%) |
| FERM-P No. 3168, NRRL B-11087 | 3.0 | (0%) | 1.6 | (83%) | 0.6 (100%) |
| FERM-P No. 3660, NRRL 11091 | 3.0 | (0%) | 1.3 | (97%) | 1.2 (97%) |

EXAMPLE 7

An Erlenmeyer flask provided with a baffle and containing 100 ml of medium A was inoculated with strain FERM-P No. 3166, (NRRL B-11086), FERM-P No. 3657 (NRRL B-11088), FERM-P No. 3658 (NRRL 11089), FERM-P No. 3167 (ATCC 31300), FERM-P No. 3659 (NRRL 11090) and FERM-P No. 3170 (ATCC 31302) from a 2-10 day old agar slant culture and cultivated for 24-72 hours under the same conditions as described in Example 2. The culture broth was centrifuged for 10 minutes while cooling, the separated cells were washed twice with phosphate buffer (pH 7.0) containing 0.85% sodium chloride and then suspended in 100 ml of this buffer. The cell suspension was treated in 5 ml portions with DL-α-hydroxycarboxylic acid so that the concentration amounted to 20 mg/ml. The mixture was incubated at 27° C. for 20 minutes. The activity of each organism for the various substrates was ascertained by the foregoing spectrophotometric analysis of the correspondingly resulting 2-oxocarboxylic acids. The results are given in the following Table in which the reactivity is expressed as the relative reactivity compared with the substrate DL-2-hydroxy-4-methylvaleric acid (100). The specific activity of each strain with 2-hydroxy-4-methylvaleric acid is: 5.8; 6.0; 0.95; 5.5; 3.5 and 0.54 nmol/mg protein with strains FERM-P No. 3166, 3657, 3658, 3167, 3170 or 3659.

The cell suspensions were broken up by sonication (70 W, 15 minutes) and centrifuged for 10 minutes while cooling. The supernatant obtained (crude extract), was incubated as described earlier with various substrates in a 0.02-M phosphate buffer (pH 7.0) or a 0.02-M Tris hydrochloride buffer (pH 8.0). Similar relative activities were found, although the specific activity was smaller (e.g. 0.50 nmol/min/mg protein with strain No. 3657).

| FERM-P No. | Relative activity in each strain | | | | | |
|---|---|---|---|---|---|---|
| Hydroxy- | 3166 | 3657 | 3658 | 3167 | 3170 | 3659 |
| acid = R | D | D | D | D | L | L |
| $CH_3-$ | — | — | 1310 | 159 | — | — |
| $CH_3CH_2-$ | 1.9 | — | 560 | 14 | 41 | — |
| $CH_3(CH_2)_2-$ | 32 | 32 | 130 | 42 | 150 | — |
| $(CH_3)_2CH-$ | 69 | 16 | 19 | 25 | — | — |
| $CH_3(CH_2)_3-$ | 72 | 68 | 194 | 59 | 39 | 400 |
| $(CH_3)_2CHCH_2-$ | 100 | 100 | 100 | 100 | 100 | 100 |
| $(CH_3)_3C-$ | — | — | — | — | — | 71 |
| $CH_3(CH_2)_4-$ | 120 | 133 | 200 | 80 | 30 | 1220 |
| $CH_3(CH_2)_5-$ | 68 | 79 | 160 | 49 | 13 | 693 |
| $CH_3(CH_2)_6-$ | 52 | 55 | 53 | 25 | 12 | 250 |
| $CH_3(CH_2)_7-$ | 39 | 13 | 23 | 6.5 | 6.8 | — |
| $CH_3(CH_2)_9-$ | 3.5 | 0.6 | 14 | 6.3 | 0.9 | — |
| $CH_3(CH_2)_{13}-$ | 3.4 | — | — | 14 | — | — |

Substrate: 
$$R-\underset{\underset{OH}{|}}{\overset{(DL)}{C}H}-COOH$$

EXAMPLE 8

An Erlenmeyer flask containing 100 ml of medium A and provided with a baffle was inoculated with *Brevibacterium albidum* NRS-130KH20B (FERM-P No. 3657, NRRL B-11088) from a slant culture and cultivated for 24 hours under the same conditions as described in Example 2. The culture broth (90 ml) was added to 22 ml of sterilised 50% glycerine, suspended and stored at −190° C. in liquid nitrogen.

An Erlenmeyer flask containing 100 ml of the medium B and provided with a baffle was inoculated by the addition of 2 ml of the foregoing thawed cell suspension and cultivated for 24 hours under identical conditions. 8.8 g of sodium DL-2-hydroxy-4-methylvalerate were added to this culture as the substrate and the fermentation was continued. 72 and 120 hours after the addition of the substrate, the remaining amount of the substrate in the broth, the optical purity (expressed in % of the D-enantiomer) and the amount of 4-methyl-2-oxovaleric acid obtained were ascertained by the methods described earlier. The results are given in the following Table:

| | Upon addition of the substrate | 72 hours | 120 hours |
|---|---|---|---|
| 2-Hydroxy-4-methyl-valeric acid (mg/ml) | 75 | 41 | 39 |
| Optical purity of the D-enantiomer in % | 0 | 85 | 100 |
| 4-Methyl-2-oxo-valeric acid (mg/ml) | 0 | 32 | 33 |

EXAMPLE 9

A 1 liter glass fermentor containing 300 ml of medium B was sterilised, inoculated with 6 ml of the cell suspension No. 3657 prepared as described in Example 8 and cultivated for 16 hours at 27° C. under aerobic conditions (air current 0.5 liter/minute, 300 revolutions/minute). 24.6 g of sodium 2-hydroxy-4-methylvalerate were added as the substrate and the pH of the culture was adjusted to 8.5 by the addition of 2-N hydrochloric acid. The fermentation was continued at pH 8.5 under the same conditions (air current 0.3 liter/minute, 300 revolutions/minute). The analysis of the substrate, 72 and 120 hours after substrate addition, is given in the following Table:

| | Upon addition of the substrate | 72 hours | 120 hours |
|---|---|---|---|
| 2-hydroxy-4-methyl-valeric acid (mg/ml) | 70 | 39 | 35 |
| Optical purity of the D-enantiomer in % | 0 | 89 | 98 |
| 4-Methyl-2-oxovaleric acid (mg/ml) | 0 | 36 | 36 |

EXAMPLE 10

A 500 ml Erlenmeyer flask provided with a baffle and containing 100 ml of medium B was inoculated with 1 ml of a cell suspension of *B. albidum* NRS-130KH20B (FERM-P No. 3657, NRRL B-11088) and cultivated for 24 hours at 27° C. while stirring and under the conditions described in Example 2. 1.48 g of sodium DL-α-hydroxy-3-pyridylacetate were then added and the fermentation was continued for 120 hours. The culture broth (pH 9.2) was centrifuged and passed through a column containing 71 ml of Dowex-1×4 (acetate form, 200–400 mesh). The anion exchanger was then washed with water and eluted with 2-N acetic acid/methanol (1:1, v/v). The eluate was controlled by thin-layer chromatography [plate: silica gel, solvent: ethyl acetate/acetic acid/water/methanol (10:2:1:2, v/v), detection: UV-light]. The fractions having UV-absorption spot (Rf 0.12) were combined and concentrated under reduced pressure. The residue was dissolved in 20 ml of water and lyophilised to give 793 mg of powder. After crystallisation from methanol/ethyl acetate, there were obtained 625 mg of optically active α-hydroxy-3-pyridylacetic acid in the form of colourless crystals of melting point 140° C.; $[\alpha]_D^{24} = -119°$ (c=1 in water); molecular formula: $C_7H_7NO_3$.

The column was then eluted with 1-N hydrochloric acid/acetic (1:1, v/v). The eluate was controlled by the same thin-layer chromatography system as described in the preceding paragraph. The fractions having UV-absorption spot (Rf 0.37) were combined, diluted with water and then added to a column containing 30 ml of Dowex-50 (H+ form). The column was washed with water and eluted with 1% aqueous ammonia. The eluate was concentrated under reduced pressure, lyophilised and the resulting powder was crystallised from methanol. There were obtained 362 mg of α-oxo-3-pyridylacetic acid in the form of colourless crystals of melting point 177°–179° C. (decomposition); molecular formula: $C_7H_5NO_3$.

EXAMPLE 11

A 500 ml Erlenmeyer flask provided with a baffle containing 100 ml of medium B was inoculated with 2 ml of a cell suspension of B. albidum NRS-130KH20B (FERM-No. 3657, NRRL B-11088) prepared according to Example 8 and cultivated for 24 hours at 27° C. while shaking (180 movements/minute). The culture broth was centrifuged for 10 minutes, the separated cells were washed three times with 100 ml of 0.02-M phosphate buffer (pH 7.5) containing 0.85% sodium chloride and then suspended in 100 ml of the same buffer. 50 ml of this suspension were decanted into a 500 ml Erylenmeyer flask, treated with 1.14 g of sodium DL-2-hydroxyoctanoate and the flask was shaken at 27° C. for 48 hours. The cells were removed from the mixture by centrifugation, the supernatant was acidified to pH 1.5 by the addition of 50% sulphuric acid and extracted three times with 50 ml of diethyl ether. The combined ether extracts were washed with water and evaporated under reduced pressure. The residue was treated with 26 ml of 2,4-dinitrophenylhydrazine reagent, prepared according to the method of C. D. Johnson, J. Am. Chem. Soc. 73, 5888, (1951), and the mixture was left to stand at room temperature overnight. The resulting yellow crystals were collected and recrystallised from benzene. There were obtained 761 mg of the 2,4-dinitrophenylhydrazone of 2-oxo-octanoic acid of melting point 137° C.; molecular formula: $C_{14}H_{18}N_4O_6$.

The hydrazone mother liquor was extracted twice with 50 ml of diethyl ether. The combined ether extracts were washed with a small amount of water and the pH of the aqueous layer was adjusted to 7.0 while shaking and adding 1-N sodium hydroxide. The aqueous layer was washed twice with 20 ml of diethyl ether and concentrated under reduced pressure. The concentrate was lyophilised to give 237 mg of sodium D-2-hydroxyoctanoate; $[\alpha]_D^{20} = +9.6°$ (c=2 in water).

EXAMPLE 12

The resolution of various DL-α-hydroxycarboxylic acids is carried out as described in Example 11 using the remaining cells of B. albidum NRS-130KH20B (FERM-P No. 3657, NRRL B-11088). The results are given in the following Table:

| Substrate | Amount Added (mg) | Incubation time (hours) | D-α-hydroxycarboxylic acid | | | α-ketocarboxylic acid | |
|---|---|---|---|---|---|---|---|
| | | | Yield*1 (mg) | $[\alpha]_D^{20*1}$ (c=2 in water) | Optical*2 purity (%) | Yield*3 (mg) | Melting point (°C.) |
| $CH_3(CH_2)_2\underset{OH}{\overset{|}{C}H}COOH$ | 1510 | 72 | 474 | +10.1° | 90 | 405*4 | 166.5–167 |
| $CH_3(CH_2)_3\underset{OH}{\overset{|}{C}H}COOH$ | 890 | 48 | 389 | +12.1° | 100 | 368*4 | 134 |
| $CH_3(CH_2)_4\underset{OH}{\overset{|}{C}H}COOH$ | 820 | 48 | 372 | +12.5° | 100 | 440*5 | 103–104 |
| $\underset{CH_3CH_2}{\overset{CH_3}{\diagdown}}\hspace{-4pt}CH\underset{OH}{\overset{|}{C}H}COOH$ | 840 | 72 | 200 | +8.9° | 96 | 619*4 | 169–171 |

*1 as the sodium salt
*2 ascertained by gas chromatography
*3 as the 2,4-dinitrophenylhydrazone
*4 recrystallised from benzene
*4 recrystallized from benzene/hexane

EXAMPLE 13

The washed cell preparation prepared from 100 ml of the culture of B. albidum NRS-130KH20B (FERM-P No. 3657, NRRL B-11088) obtained according to Example 11 was again washed with distilled water and lyophilised, there being obtained 478 mg of lyophilisate (dry cell powder). The dry cell powder was suspended in 100 ml of 0.02-M phosphate buffer (pH 7.5). The mixture was treated with 2.34 g of sodium DL-2-hydroxy-4-methylvalerate and, after adjusting the pH to 7.5, shaken at 27° C. (180 movements/minute). After shaking for 48 and 72 hours, the substrate remaining in the buffer, the optical purity and the amount of 4-methyl-2-oxovaleric acid obtained was ascertained by the method described earlier. The results are given in the following Table:

| | Prior to the shaking | 48 hours | 72 hours |
|---|---|---|---|
| 2-Hydroxy-4-methyl-valeric acid (mg/ml) | 20.0 | 11.6 | 10.9 |
| Optical purity of the D-enantiomer in % | 0 | 100 | 100 |
| 4-Methyl-2-oxovaleric acid (mg/ml) | 0 | 9.6 | 9.9 |

We claim:
1. A process of obtaining an optically pure enantiomer of a D,L-α-hydroxy carboxylic acid of the formula:

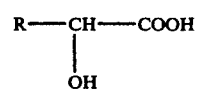

wherein R is a alkyl group containing from 1 to 13 carbon atoms or pyridine
or salts thereof
comprising enzymatically treating said D,L-α-hydroxy carboxylic acid in a fermentation medium with a microorganism belonging to the genus Streptomyces, Pseudomonas or Bacillus or to the Coryneform group which microorganism has enantiospecific dehydrogenase activity to selectively dehydrogenate only one of said enantiomers to an α-keto acid of the formula:

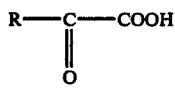

wherein R is as above,
or salt thereof,
to leave the other of said enantiomers free of said enantiomer which was selectively dehydrogenated.

2. The process of claim 1 wherein said acid is 2-hydroxypropionic acid, 2-hydroxbutyric acid, 2-hydroxyvaleric acid, 2-hydroxy-3-methylbutyric acid, 2-hydroxycaproic acid, 2-hydroxy-4-methylvaleric acid, 2-hydroxy-3,3-dimethylbutyric acid, 2-hydroxyheptylic acid, 2-hydroxy-4-methylcaproic acid, 2-hydroxycaprylic acid, 2-hydroxypelargonic acid, 2-hydroxydecanoic acid, 2-hydroxyundecanoic acid, 2-hydroxydodecanoic acid, 2-hydroxytridecanoic acid, 2-hydroxytetradecanoic acid, 2-hydroxypentadecanoic acid or α-hydroxy-3-pyridylacetic acid.

3. The process of claim 1 wherein said microorganism is the strain Bacillus megaterium FERM-P No. 3164, NRRL B-11084; Bacillus FERM-P No. 3165, NRRL 11085; Bacillus freudenreichii FERM-P No. 3169, ATCC 31301; one of the strains FERM-P No. 3166, NRRL B-11086; FERM-P No. 3167, ATCC 31300; FERM-P No. 3657, NRRL B-11088; or FERM-P No. 3168, NRRL B-11087 belonging to the Coryneform group; Pseudomonas fluorescens FERM-P No. 3658, NRRL 11089; Pseudomonas putida FERM-P No. 3172, ATCC 31303 or No. 3659, NRRL 11090; Pseudomonas FERM-P No. 3170, ATCC 31302, Streptomyces FERM-P No. 3160 (NRS-79KH-1A), NRRL 11083 or FERM-P No. 3660 (NRS-125KH-27A), NRRL 11091 is used as the microorganism.

4. A process for separating D,L-α-hydroxycarboxylic acid of the formula:

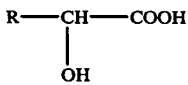

wherein R is an alkyl group containing from 1 to 13 carbon atoms or pyridine
or salts thereof
into an optical pure enantiomer thereof comprising enzymatically treating said DL-α-hydroxy carboxylic acid in a fermentation medium with a microorganism belonging to the genus Streptomyces, Pseudomonas or Bacillus or to the Coryneform group which microorganism has enantiospecific dehydrogenase activity, to selectively dehydrogenate only one of said enantiomers to an α-keto acid of the formula:
wherein R is as above isolating the remaining enantiomer of the α-hydroxy carboxylic acid as pure enantiomers from said fermentation medium.

5. The process of claim 4 wherein said α-hydroxy carboxylic acid is 2-hydroxypropionic acid, 2-hydroxybutyric acid, 2-hydroxyvaleric acid, 2-hydroxy-3-methylbutyric acid, 2-hydroxycaproic acid, 2-hydroxy-4-methylvaleric acid, 2-hydroxy-3,3-dimethylbutyric acid, 2-hydroxyheptylic acid, 2-hydroxy-4-methylcaproic acid, 2-hydroxycaprylic acid, 2-hydroxypelargonic acid, 2-hydroxydecanoic acid, 2-hydroxyundecanoic acid, 2-hydroxydodecanoic acid, 2-hydroxytridecanoic acid, 2-hydroxytetradecanoic acid, 2-hydroxypentadecanoic acid or α-hydroxy-2-pyridylacetic acid.

6. A process of claim 4 wherein said microorganism is the strain Bacillus megaterium FERM-P No. 3164, NRRL B-11084; Bacillus FERM-P No. 3165, NRRL 11085; Bacillus freudenreichii FERM-P No. 3169, ATCC 31301; one of the strains FERM-P No. 3166, NRRL B-11086; FERM-P No. 3167, ATCC 31300; FERM-P No. 3657, NRRL B-11088; or FERM-P No. 3168, NRRL B-11087 belonging to the Coryneform group; Pseudomonas fluorescens FERM-P No. 3658, NRRL 11089; Pseudomonas putida FERM-P No. 3172, ATCC 31303 or No. 3659, NRRL 11090; Pseudomonas FERM-P No. 3170, ATCC 31303 Streptomyces FERM-P No. 3160 (NRS-79K-1A), NRRL 11083 or FERM-P No. 3660 (NRS-125KH-27A), NRRL 11091.

7. A process of producing an optically pure enantiomer of D,Lα-hydroxycarboxylic acid of the formula:

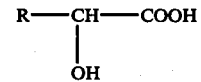

wherein R is alkyl containing 1 to 13 carbon atoms or pyridine;
or salts thereof;
comprising utilizing as a starting material said D,L-α-hydroxycarboxylic acid, enzymatically treating said starting material in a fermentation medium with a microorganism belonging to the genus Streptomyces, Pseudomonas or Bacillus or to the Coryneform group, which microorganism has enantiospecific dehydrogenase activity to selectively dehydrogenate only one of said enantiomers to an α-keto acid of the formula:

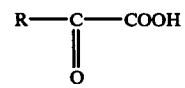

wherein R is as above,
or salt thereof;
isolating the remaining enantiomer of said α-hydroxycarboxylic acid and said α-ketocarboxylic acid from said fermentation medium, hydrogenating said isolated α-ketocarboxylic acid to form D,L-α-hydroxy carboxylic acid and utilizing said D,L-α-hydroxycarboxylic acid as said starting material.

8. The process of claim 4 said α-hydroxycarboxylic acid wherein 2-hydroxypropionic acid, 2-hydroxybutyric acid, 2-hydroxyvaleric acid, 2-hydroxy-3-methylbutyric acid, 2-hydroxycaproic acid, 2-hydroxy-4-methylvaleric acid, 2-hydroxy-3,3-dimethylbutyric acid, 2-hydroxyheptylic acid, 2-hydroxy-4-methylcaproic acid, 2-hydroxycaprylic acid, 2-hydroxypelargonic acid, 2-hydroxydecanoic acid, 2-hydroxyundecanoic acid, 2-hydroxydodecanoic acid, 2-hydroxytridecanoic acid, 2-hydroxytetradecanoic acid, 2-hydroxypentadecanoic acid or α-hydroxy-3-pyridylacetic acid.

9. The process of claim 4 wherein the microorganism is the strain *Bacillus megaterium* FERM-P No. 3164, NRRL B-11084; Bacillus FERM-P No. 3165, NRRL 11085; *Bacillus freudenreichii* FERM-P No. 3169, ATCC 31301; one of the strains FERM-P No. 3166, NRRL B-11086; FERM-P No. 3167, ATCC 31300; FERM-P No. 3657, NRRL B-11088; or FERM-P No. 3168, NRRL B-11087 belonging to the Coryneform group; *Pseudomonas fluorescens* FERM-P No. 3658, NRRL 11089; *Pseudomonas putida* FERM-P No. 3172, ATCC 31303 or No. 3659, NRRL 11090; Pseudomonas FERM-P No. 3170, ATCC 31303, Streptomyces FERM-P No. 3160 (NRS-79K-1A), NRRL 11083 or FERM-P No. 3660 (NRS-125KH-27A), NRRL 11091.

* * * * *